United States Patent
Naimark et al.

(10) Patent No.: US 7,569,032 B2
(45) Date of Patent: Aug. 4, 2009

(54) MEDICAL DEVICE FOR DELIVERY OF A BIOLOGICALLY ACTIVE MATERIAL TO A LUMEN

(75) Inventors: Wendy Naimark, Cambridge, MA (US); Maria Palasis, Wellesley, MA (US); Robbert A Herrmann, Boston, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 541 days.

(21) Appl. No.: 10/645,652

(22) Filed: Aug. 20, 2003

(65) Prior Publication Data

US 2004/0044308 A1 Mar. 4, 2004

Related U.S. Application Data

(63) Continuation of application No. 09/724,505, filed on Nov. 28, 2000, now Pat. No. 6,638,246.

(51) Int. Cl.
*A61M 31/00* (2006.01)
(52) U.S. Cl. .................................. 604/103.01
(58) Field of Classification Search ............ 604/164.01, 604/264, 507, 191, 500, 104, 96.01, 103–103.02, 604/103.08
See application file for complete search history.

(56) References Cited

U.S. PATENT DOCUMENTS

| | | | |
|---|---|---|---|
| 4,610,249 A | 9/1986 | Makofski et al. | |
| 4,796,629 A | 1/1989 | Grayzel | |
| 5,102,132 A | 4/1992 | Chen | |
| 5,112,305 A * | 5/1992 | Barath et al. | 604/103.01 |
| 5,120,322 A | 6/1992 | Davis et al. | |
| 5,154,725 A | 10/1992 | Leopold | |
| 5,233,972 A | 8/1993 | Rattner | |
| 5,304,121 A | 4/1994 | Sahatjian | |
| 5,320,634 A | 6/1994 | Barath et al. | |
| 5,354,279 A | 10/1994 | Höfling | |
| 5,374,236 A | 12/1994 | Hassler | |
| 5,569,245 A | 10/1996 | Guglielmi et al. | |
| 5,681,281 A | 10/1997 | Vigil et al. | |

(Continued)

FOREIGN PATENT DOCUMENTS

JP 4-282146 10/1992

(Continued)

OTHER PUBLICATIONS

Michael L. Reed et al., *Micromechanical Devices for Intravascular Drug Delivery*, Journal of Pharmaceutical Sciences, vol. 87, No. 11, Nov. 1998.

Primary Examiner—Kevin C Sirmons
Assistant Examiner—Catherine N Witczak
(74) Attorney, Agent, or Firm—Fish & Richardson P.C.

(57) ABSTRACT

An apparatus for delivery of biologically active materials comprises a catheter and balloon having micro-needles or pores. In the apparatus, the balloon can have a polymer coating containing the biologically active material, and the apparatus can include a sheath surrounding the balloon. In one embodiment the biologically active material is delivered through lumens in the micro-needles. Another embodiment of the invention is an apparatus for delivery of biologically active materials comprising a catheter with a balloon disposed thereon and a shockwave generator for producing a shockwave for delivering the biologically active material to a body lumen. Methods for delivery of biologically active materials are also disclosed.

11 Claims, 11 Drawing Sheets

U.S. PATENT DOCUMENTS

| | | | |
|---|---|---|---|
| 5,693,029 A * | 12/1997 | Leonhardt | 604/264 |
| 5,713,863 A * | 2/1998 | Vigil et al. | 604/104 |
| 5,725,494 A | 3/1998 | Brisken | |
| 5,746,968 A | 5/1998 | Radisch, Jr. | |
| 5,865,796 A | 2/1999 | McCabe | |
| 5,941,868 A | 8/1999 | Kaplan et al. | |
| 6,001,069 A | 12/1999 | Tachibana et al. | |
| 6,096,000 A | 8/2000 | Tachibana et al. | |
| 6,102,904 A | 8/2000 | Vigil et al. | |
| 6,135,976 A | 10/2000 | Tachibana et al. | |
| 6,197,013 B1 | 3/2001 | Reed et al. | |
| 6,210,392 B1 | 4/2001 | Vigil et al. | |
| 6,334,856 B1 | 1/2002 | Allen et al. | |
| 6,565,532 B1 * | 5/2003 | Yuzhakov et al. | 604/142 |
| 6,638,246 B1 * | 10/2003 | Naimark et al. | 604/103 |

FOREIGN PATENT DOCUMENTS

| | | |
|---|---|---|
| JP | 5-505132 | 8/1993 |
| JP | 90-28665 | 2/1997 |
| JP | 11-009701 | 1/1999 |
| JP | 11-225985 | 8/1999 |
| JP | 11-509123 | 8/1999 |
| WO | 92/11890 | 7/1992 |
| WO | 95/03083 | 2/1995 |
| WO | 97/03718 | 2/1997 |
| WO | 98/48711 | 11/1998 |
| WO | WO 98/48711 | 11/1998 |
| WO | WO 99/33391 | 7/1999 |
| WO | 99/38559 | 8/1999 |
| WO | WO 99/38559 | 8/1999 |
| WO | WO 99/64580 | 12/1999 |
| WO | WO 00/00095 | 1/2000 |
| WO | 00/07508 | 2/2000 |
| WO | WO 00/07508 | 2/2000 |
| WO | WO 00/16704 | 3/2000 |
| WO | WO 00/18468 | 4/2000 |
| WO | 00/66199 | 11/2000 |
| WO | 02/43796 | 6/2002 |

* cited by examiner

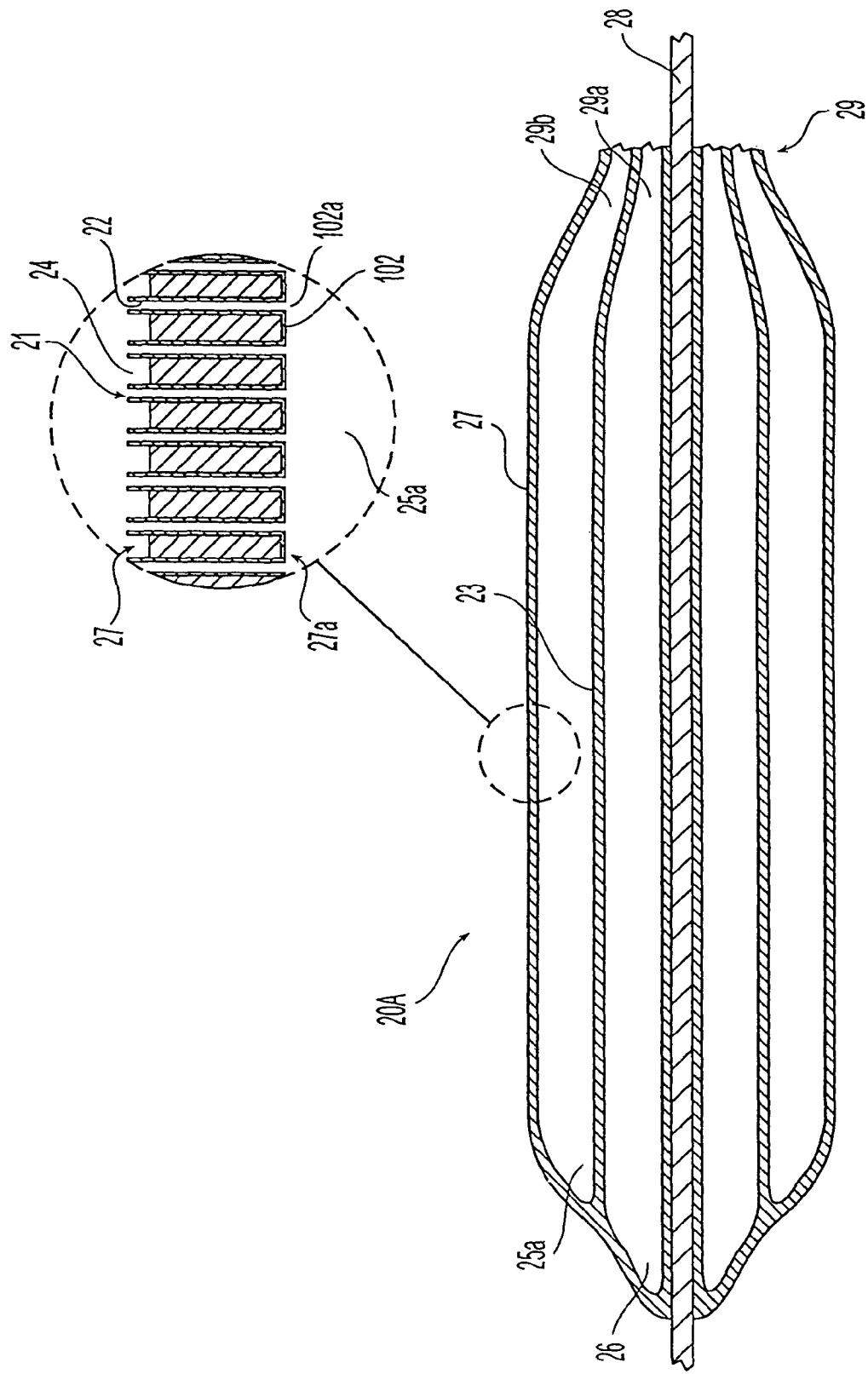

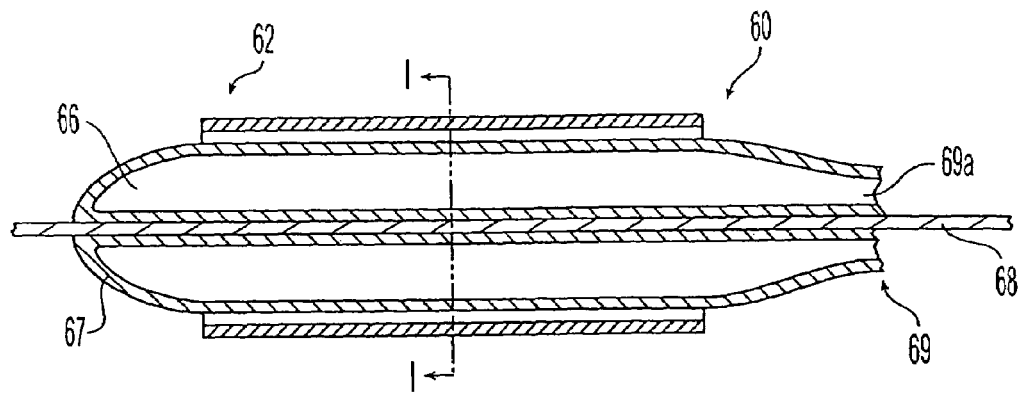
*Fig. 6A*
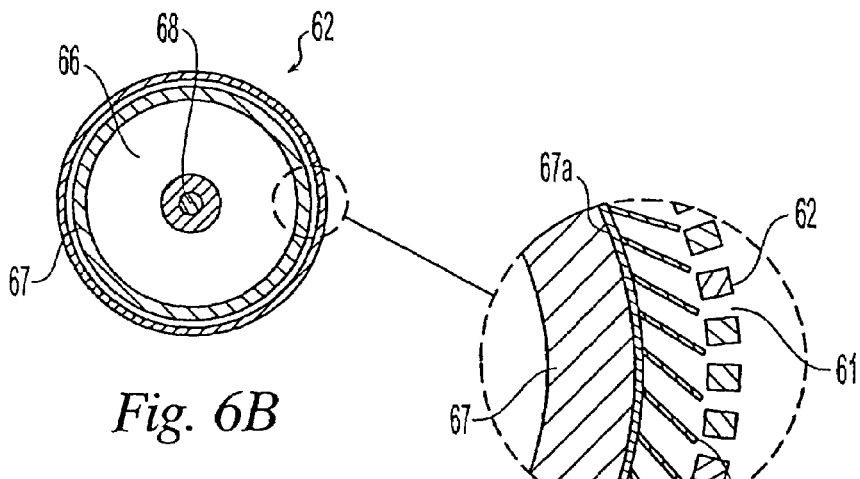
*Fig. 6B*
*Fig. 6B'*
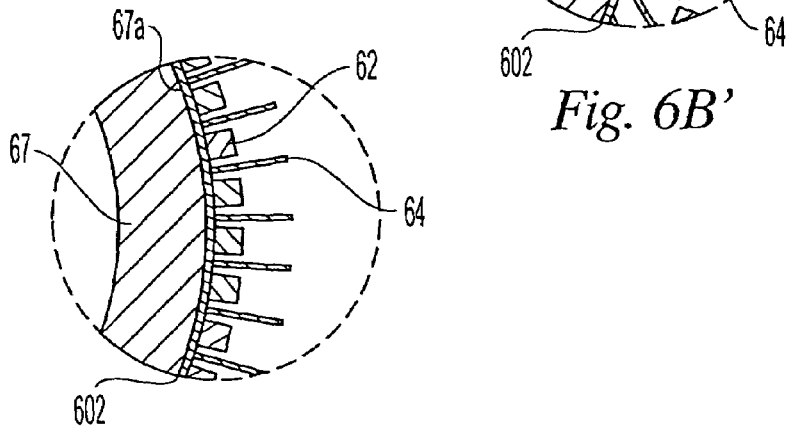
*Fig. 6C*

MEDICAL DEVICE FOR DELIVERY OF A BIOLOGICALLY ACTIVE MATERIAL TO A LUMEN

CROSS-REFERENCE TO RELATED APPLICATION

This application is a continuation application of U.S. patent application Ser. No. 09/724,505, filed Nov. 28, 2000, now U.S. Pat. No. 6,638,246 now allowed, and incorporated herein in its entirety by reference.

FIELD OF THE INVENTION

This invention relates generally to medical devices and methods for delivering a biologically active material to a desired location within the body of a patient. More particularly, the invention is directed to medical devices having a catheter and a balloon with a plurality of micro-needles at its outer surface for delivering a biologically active material to a body lumen. Additionally, the invention is directed to medical devices having a catheter, a balloon and a sheath surrounding the balloon. Also, the invention is directed to medical devices having a catheter, a balloon and a shockwave generator for delivery of biologically active materials.

BACKGROUND OF THE INVENTION

When a disease is localized to a particular part of the body, in particular a body lumen, such as, without limitation, a blood vessel, direct administration of biologically active materials for the treatment of the disease may be more preferred than systemic administration. Systemic administration requires larger amounts and/or higher concentrations of the biologically active materials because of inefficiencies associated with the indirect delivery of such materials to the afflicted area. Also, systemic administration may cause side effects which may not be a problem when the biologically active material is locally administered.

However, such localized delivery of biologically active materials to a body lumen is difficult since body lumens are involved in the transport of body fluids, which tend to carry the biologically active material away from the afflicted area. Thus, there is a need for devices and methods for the localized delivery of biologically active materials to afflicted tissue, especially body lumens.

A number of devices for delivering biologically active materials to body lumens or vessels involve the use of catheters having expandable portions, such as a balloon, disposed on the catheter. To overcome the problem that the delivered biologically active material is washed away from the applied area by the blood-flow, there are generally two kinds of prior art balloon catheters: one kind is a balloon catheter which temporarily occludes blood-flow and infuses a biologically active material to the occluded area, and the other kind is a balloon catheter which directly administers the biologically active material to a vessel wall by the use of macro-needles. However, the former still has the problem of systemic leakage around the balloon, allowing for systemic distribution of the biologically active material. On the other hand, although the latter type of balloon catheters do not cause significant systemic leakage of the biologically active material, because of the large size of the macro-needles used to inject the biologically active material into the tissue, there is still back-leakage at the needle track. Also, the large size of the needles cause damage in the tissue of the vessel wall. Thus, the prior art balloon catheters cannot deliver a biologically active material quickly and accurately to a wall of body lumen without causing damage in the body lumen tissue and/or systemic leakage.

In addition, rapid advances in DNA technologies have increased the necessity for a device or method which realizes more accurate and uniform delivery of genetic materials. Therefore, there is still a need for devices and methods which cause minimum tissue damage while ensuring accurate and uniform localized delivery of biologically active materials including genetic materials to body lumens.

SUMMARY OF THE INVENTION

These and other objectives are accomplished by the present invention. To achieve the aforementioned objectives, we have invented a medical apparatus and a method for delivery of a biologically active material to a surface of a body lumen.

The apparatus for delivery of biologically active materials of the invention comprises a catheter and a balloon having micro-needles.

In an embodiment of the invention, the apparatus comprises a catheter, a balloon, with a biologically active material disposed on an outer surface of the balloon, and micro-needles disposed upon the outer surface of the balloon. The micro-needles contact a body lumen as the balloon is expanded, and the biologically active material is delivered into the body lumen. The biologically active material can be delivered by fluid convection along the outer surface of the micro-needles. Alternatively, biologically active material can, instead of being disposed on the outer balloon surface, be expelled from an inner compartment of the balloon through pores in the outer balloon surface. The balloon is optionally surrounded by a sheath.

In another embodiment of the invention, the apparatus comprises a catheter having at least one lumen in fluid communication with an internal compartment of the balloon, and micro-needles having a lumen in fluid communication with the compartment, wherein the micro-needles are disposed upon an outer surface of the balloon. The micro-needles contact a body lumen as the balloon is expanded, and the biologically active material is delivered to the body lumen through the micro-needle lumen. The balloon is optionally surrounded by a sheath.

Further, another embodiment of the apparatus of the invention comprises a catheter, a balloon disposed upon the catheter, and a shockwave generator for delivery of a biologically active material.

Moreover, in another embodiment, the apparatus of the invention comprises a catheter, a balloon having micro-needles disposed upon or within an outer surface of the balloon, and a triggering source for rupturing the micro-needles. The micro-needles are ruptured by the triggering source, which can be a shockwave, and a biologically active material is delivered through the micro-needles to an afflicted area of a body lumen.

The present invention also includes a method for delivering a biologically active material to a body lumen. In one embodiment, the method is carried out by inserting a catheter with a balloon disposed thereon into a body lumen. The balloon has micro-needles disposed upon or within its outer surface. Once the catheter is inserted, the balloon is inflated so that the micro-needles contact the surface of the body lumen. The biologically active material is then delivered to the surface of the body lumen.

In another embodiment, the method of the invention involves inserting a catheter having a balloon disposed upon it into a body lumen. The balloon is inflated to contact a body lumen. A shockwave is then applied to the afflicted area of the body lumen to allow delivery of the biologically active material into the body lumen.

DESCRIPTION OF THE FIGURES

FIGS. 2A and 2B depict cross-sectional views along the longitudinal axis of embodiments of a balloon catheter of the invention, wherein hollow micro-needles with apertures are disposed upon a plate which is disposed on a balloon surface or within the balloon wall. The catheter has a lumen for containing the biologically active material and another lumen for inflating the balloon. Details of the micro-needles are shown in the enlarged portion of the balloon.

In FIG. 4A, the micro-needles are disposed upon a porous plate, and the plate is attached to the inner surface of the balloon wall. In FIG. 4B, the micro-needles may be mounted on a solid plate and the solid plate is attached to the inner surface of the balloon wall. Details of the micro-needles are shown in the enlarged portions of the balloon.

In FIG. 5A, the balloon is in its deflated state. In FIG. 5B, the balloon is in its inflated state. Details of the micro-needles are shown in the enlarged portions of the balloon.

FIG. 6A depicts a cross-sectional view along the longitudinal axis of another embodiment of a balloon catheter of the invention in its deflated state, wherein a sheath surrounds a balloon having solid micro-needles. FIG. 6B depicts a cross-sectional view of the same embodiment which is cut along the line I-I in FIG. 6A. A portion of the FIG. 6B is enlarged to FIG. 6B'. FIG. 6C shows the same portion as in FIG. 6B' and the balloon is in its inflated state.

In FIG. 7A, the balloon is in deflated state, and in FIG. 7B, the balloon is in its inflated state.

DESCRIPTION OF THE PREFERRED EMBODIMENTS

The medical apparatus suitable for the present invention include those having at least an inflatable portion such as a balloon. The term "balloon" is defined as an inflatable bag-like object made of a balloon wall. The balloon wall may be made of one or more layers. The balloon may contain one or more internal walls in addition to the balloon wall. Also, the balloon can have more than one compartment.

Figure 1:
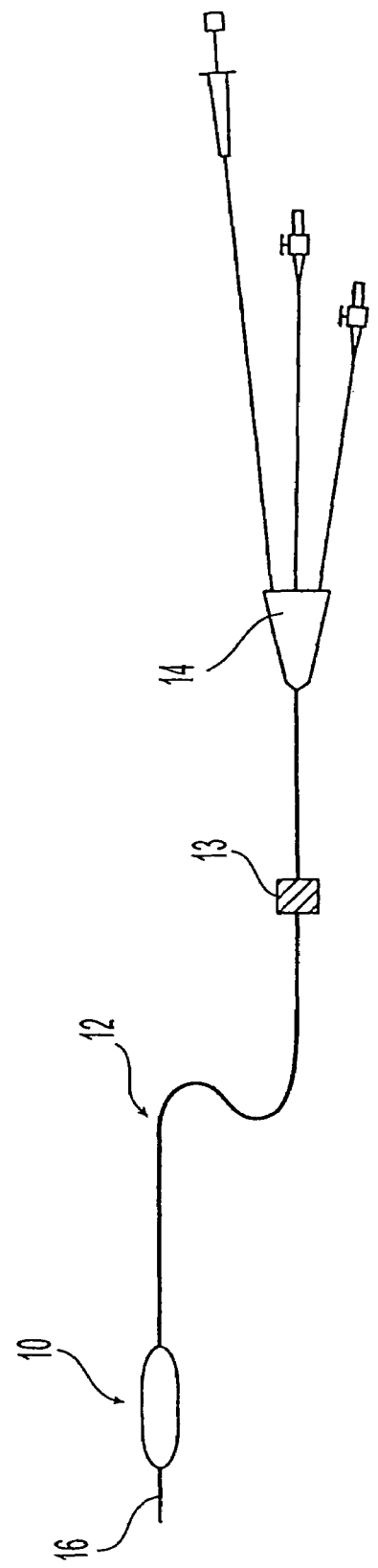
FIG. 1 illustrates a configuration of an embodiment of a balloon catheter of the invention.

A configuration of an embodiment of an apparatus of the present invention is illustrated in FIG. 1. The embodiment includes a catheter 12 which has a proximal end 14 and distal end 16 and includes a guide wire and a lumen for inflation (both not shown in FIG. 1). A balloon 10 with micro-needles (not shown) disposed upon its outer surface is located upon the distal portion 16 of the catheter 12. Also, the balloon catheter can include a shockwave generator 13 disposed upon the proximal portion 14 of the catheter 12. Once the catheter is introduced into a body lumen in a manner known to the skilled artisan, the balloon is positioned to a targeted area in the body lumen and then inflated to contact a surface of the body lumen in a way known in the art. After a biologically active material is delivered, the balloon is deflated and removed.

Figure 2B:
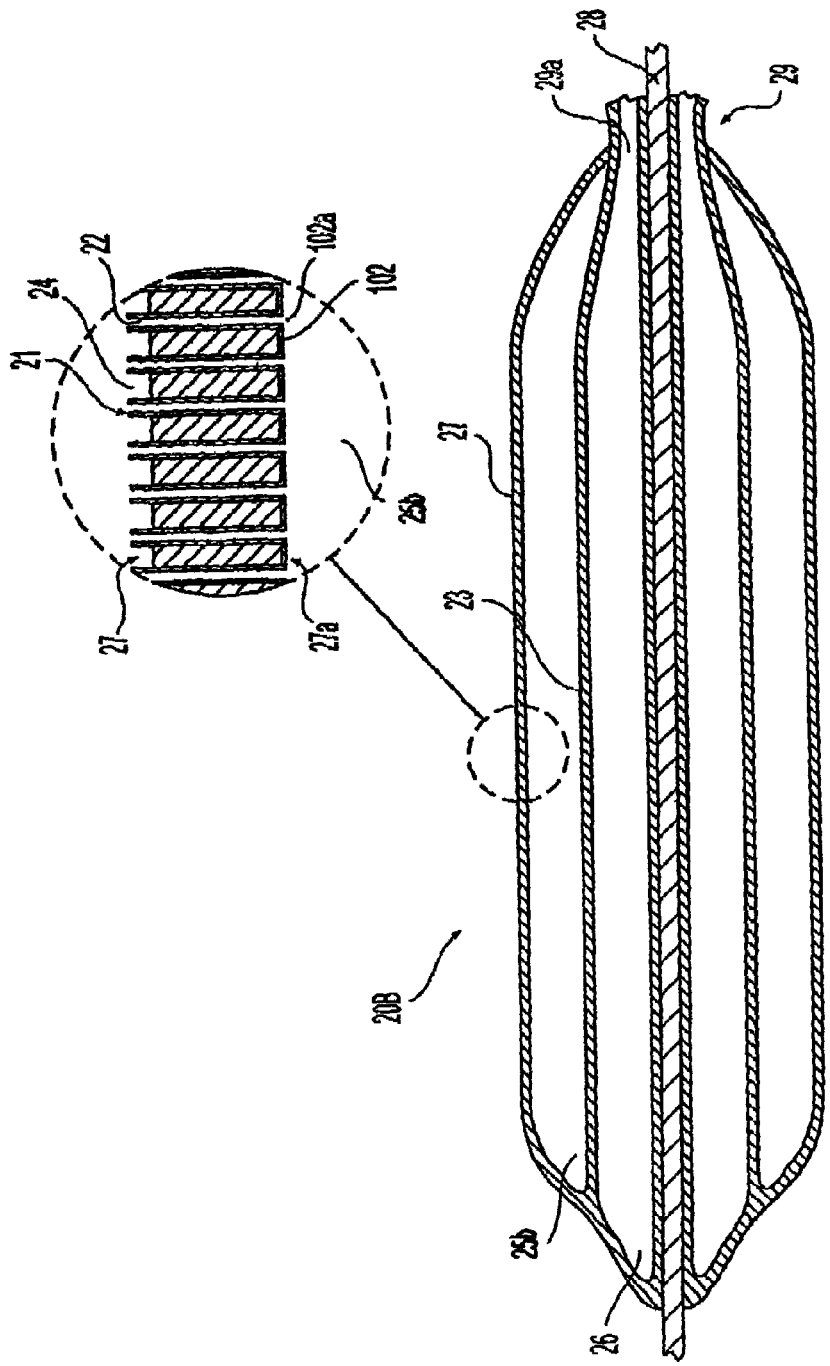

FIGS. 2A and 2B show two embodiments of the present invention. A balloon 20A in FIG. 2A is disposed upon a catheter 29 having a guidewire 28. The balloon 20A is made of a balloon wall 27 having an inner and outer surface and has an internal wall 23, an inflation compartment 26, and an internal compartment 25a surrounded by the balloon wall 27 and the internal wall 23. A plate 102, having pores 102a and a plurality of micro-needles 21 disposed upon it, is positioned on the inner surface 27a of the balloon wall 27. The micro-needles 21 project through the balloon wall 27 and are disposed on the outer surface of the balloon 27b. It should be noted that the micro-needles do not have to be actually resting on the outer surface in order to be considered as being disposed thereon. As long as the micro-needles protrude through or from the surface, they are considered as being disposed upon the surface. The micro-needles 21 have an aperture 24 and a lumen 22. The lumen 22 is aligned with the pores 102a such that the lumen 22 is in fluid communication with the interior compartment 25a of the balloon 20A. The interior compartment 25a can be in fluid communication with a lumen 29b of the catheter 29.

The term "micro-needle" is a term of art. Generally, a "micro-needle" is construed as a needle having a diameter at most about 100 μm, preferably about 10 μm or less and a length at most about 1 mm. The micro-needles applicable to this invention include hollow ones 21 such as those in FIG. 2A. The term "hollow" means having one or more lumen(s) 22 running through the interior of the micro-needle 21, wherein fluid and/or solid materials can pass through the lumen(s) 22. These hollow micro-needles 21 can preferably have an aperture 24 connected to the lumen 22 of the micro-needle 21. The term "aperture" means an opening in the outer surface of the micro-needle 21 which are sufficiently large to allow passage of fluid and/or solid materials out of the micro-needles. The aperture can be at the tip of the micro-needles or located at other places in the micro-needle outer surface. In other embodiments as discussed below, the micro-needles can be solid or capable of being ruptured.

In the embodiment shown in FIG. 2A, the balloon 20A is inflated by infusing a liquid or gas into the inflation compartment 26 of the balloon 20A using inflation lumen 29a of the catheter 29. As the balloon 20A is inflated, the micro-needles 21 contact a surface of the body lumen, and a biologically active material located in the interior balloon compartment 25a is delivered through the micro-needle lumens 22 and aperture 24 to the body lumen. The biologically active material is delivered, quickly and accurately without systemic leakage. After the delivery is completed, the balloon 20A is deflated and removed from the body lumen. In other embodiments, the lumen 29b for the biologically active material and the inflation lumen 29a can be the same; and/or the inflation compartment 26 and the interior compartment 25a containing the biologically active material can be the same.

FIG. 2B shows another embodiment, a balloon 20B, which is similar to the balloon 20A in FIG. 2A, except that the interior compartment 25b is not connected to a catheter lumen. In this embodiment, the interior compartment 25b contains the biologically active material, and expansion of the inflation compartment 26 will squeeze the biologically active material out of the interior compartment 25b through the micro-needles 21 into the body lumen surface.

Figure 3:
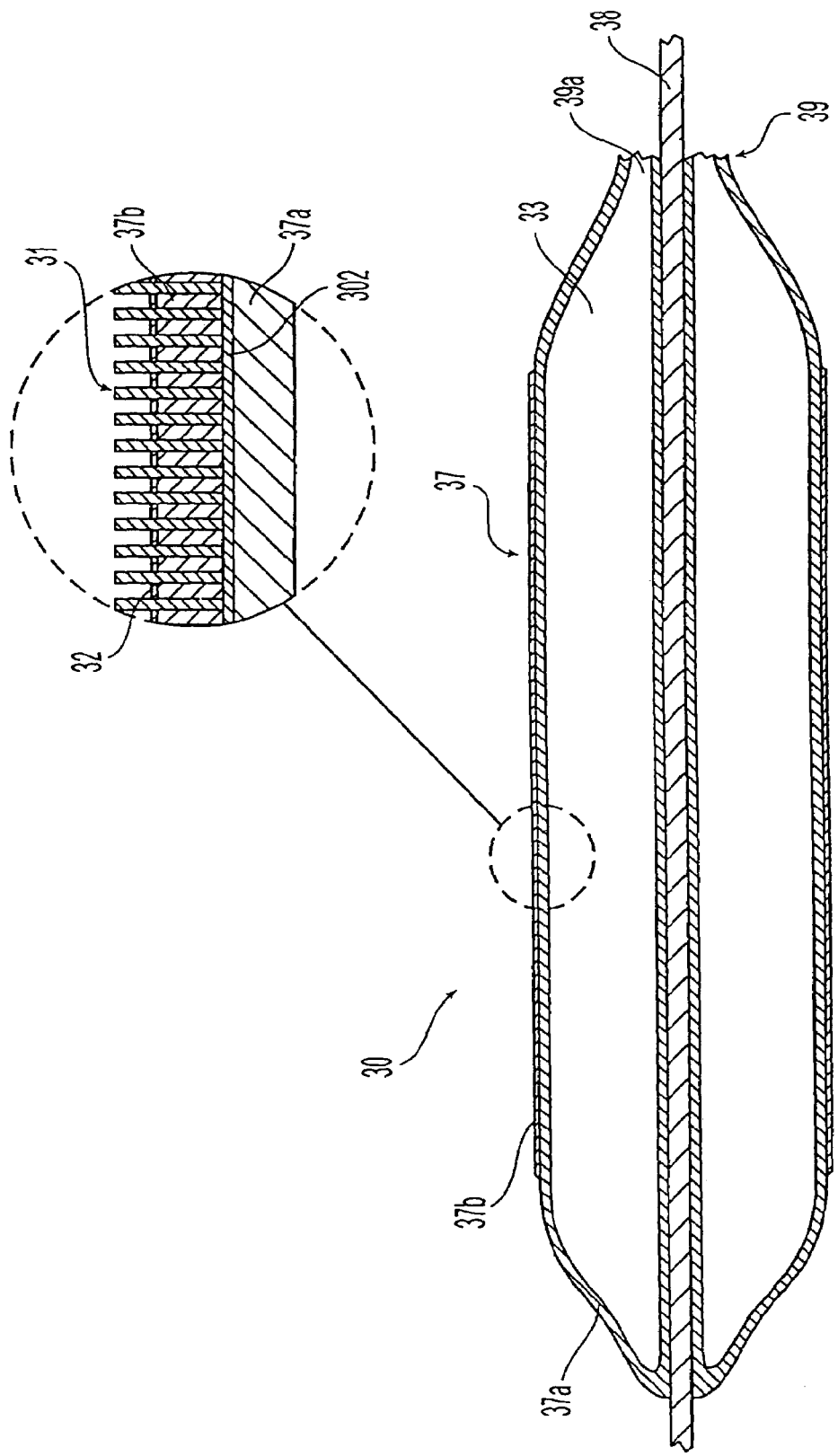
FIG. 3 depicts a cross-sectional view along the longitudinal axis of another embodiment of a balloon catheter of the invention, wherein solid micro-needles, i.e., micro-needles without lumens, are disposed upon a plate which is disposed upon a balloon surface or within the balloon wall. The outer surface of the balloon is coated with a polymer containing a biologically active material. Details of the micro-needles are shown in the enlarged portion of the balloon.

Another embodiment of the present invention is shown in FIG. 3. A balloon 30 is made of balloon wall 37, and the balloon wall is made of an outer layer 37b and an inner layer 37a. In this embodiment, a plurality of solid micro-needles 31 are disposed upon a plate 302 which is disposed between the outer layer 37b and the inner layer 37a. The micro-needles project through the outer layer 37b and are disposed on an outer surface of the balloon. The micro-needles can also be hollow in other embodiments. The outer surface of the balloon 30 is coated with a polymer containing a biologically active material 32. The balloon 30 is inflated by infusing a liquid or gas into an inflation compartment 33 using an inflation lumen 39a of the catheter 39 having a guidewire 38. The needles 31 pierce the body lumen and create micro-pores or nano-pores, i.e., spaces of the size of the micro-needle, in the body lumen. The biologically active material contained in the coating 32 is squeezed by the balloon 30 and forced into or allowed to seep into the micro- or nano-pores created by the micro-needles. After a predetermined time, the balloon 30 is deflated and removed from the body lumen. The time during which the balloon is inflated is determined by the type of body lumen tissue, the biologically active material used, carrier material or coating if used and the size and number of needles. For example, if the body lumen is a coronary artery, the time is generally between about 5 seconds and about 2 minutes, preferably between about 10 and about 30 seconds.

Figure 4A:
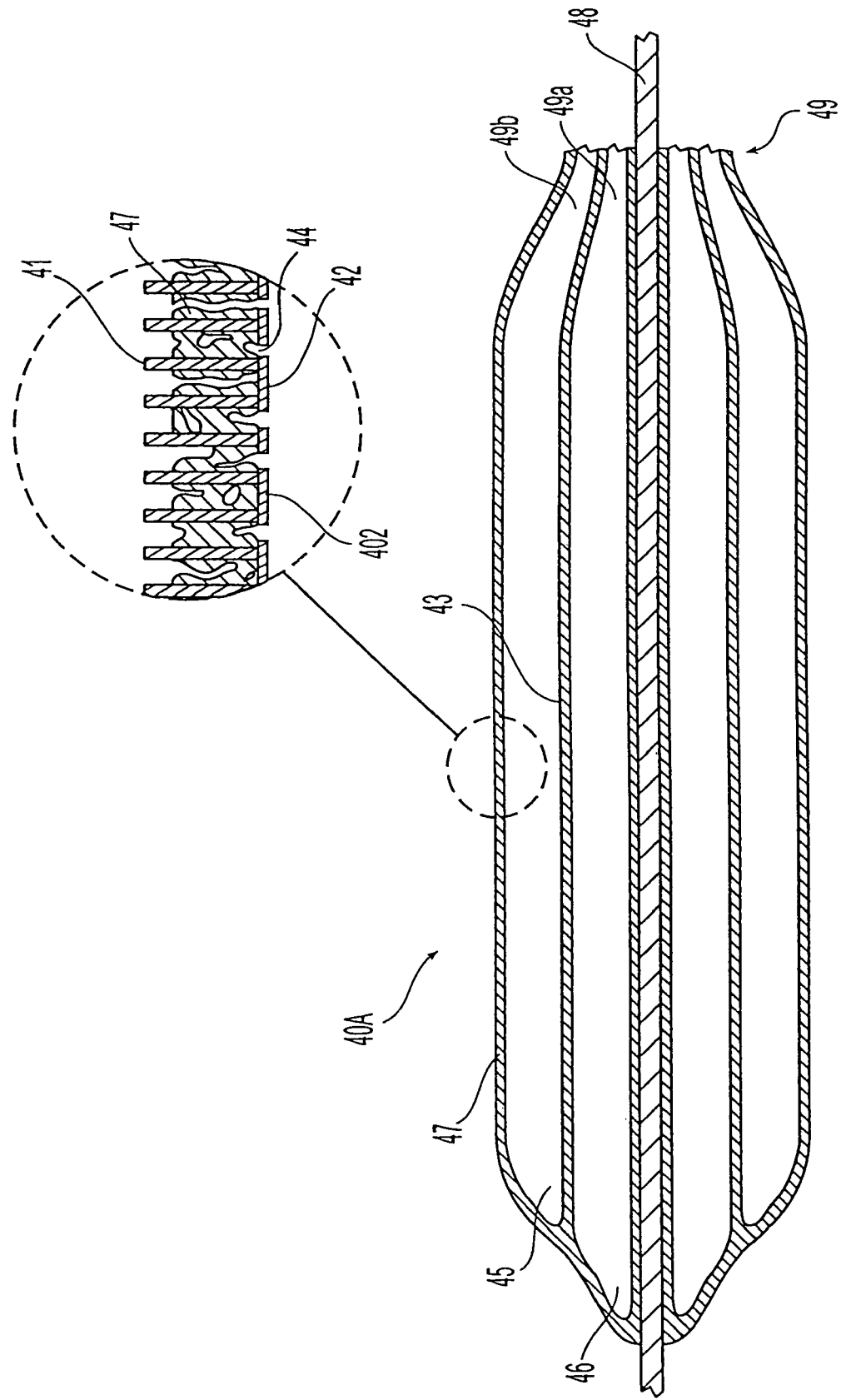
FIGS. 4A and 4B depict a cross-sectional view along the longitudinal axis of another embodiment of a balloon catheter of the invention, wherein solid micro-needles are disposed upon a plate which is disposed upon a balloon surface or within the balloon wall and the micro-needles project through a porous outer surface of the balloon.

FIG. 4A shows another embodiment of an apparatus of the present invention. A plurality of solid micro-needles 41 are disposed upon a porous plate 402, which is disposed on a porous balloon wall 47 of the balloon 40A. In some embodiments, the needles can be hollow. The porous plate 402 has a plurality of pores 44, and the porous balloon wall 47 has a plurality of pores 42. The balloon 40A also includes an interior compartment 45 defined by an internal wall 43. The balloon 40A of this embodiment is inflated in a body lumen by inserting a liquid or gas into an inflation compartment 46 using an inflation lumen 49a of the catheter 49 having a guidewire 48. Upon inflation, the micro-needles 41 contact a surface of the body lumen piercing the surface and create micro- or nano-pores in the surface. Then, a biologically active material, which is placed into the interior compartment 45 of the balloon 40A using a first catheter lumen 49b, is expelled from the interior compartment 45 through the pores 44 of the plate 402 and the pores 42 of the balloon wall 47. The biologically active material is delivered into the micro- or nano-pores created by the micro-needles 41. After the biologically active material is delivered, the balloon is deflated and removed from the body lumen.

In the other embodiments, the interior compartment 45 is not in fluid communication with catheter lumen 49b. Instead, the interior compartment 45 contains the biologically active material, and expansion of the inflation compartment 46 will squeeze the biologically active material out of the interior compartment 45 through the pores 42 and pores 44.

Figure 4B:
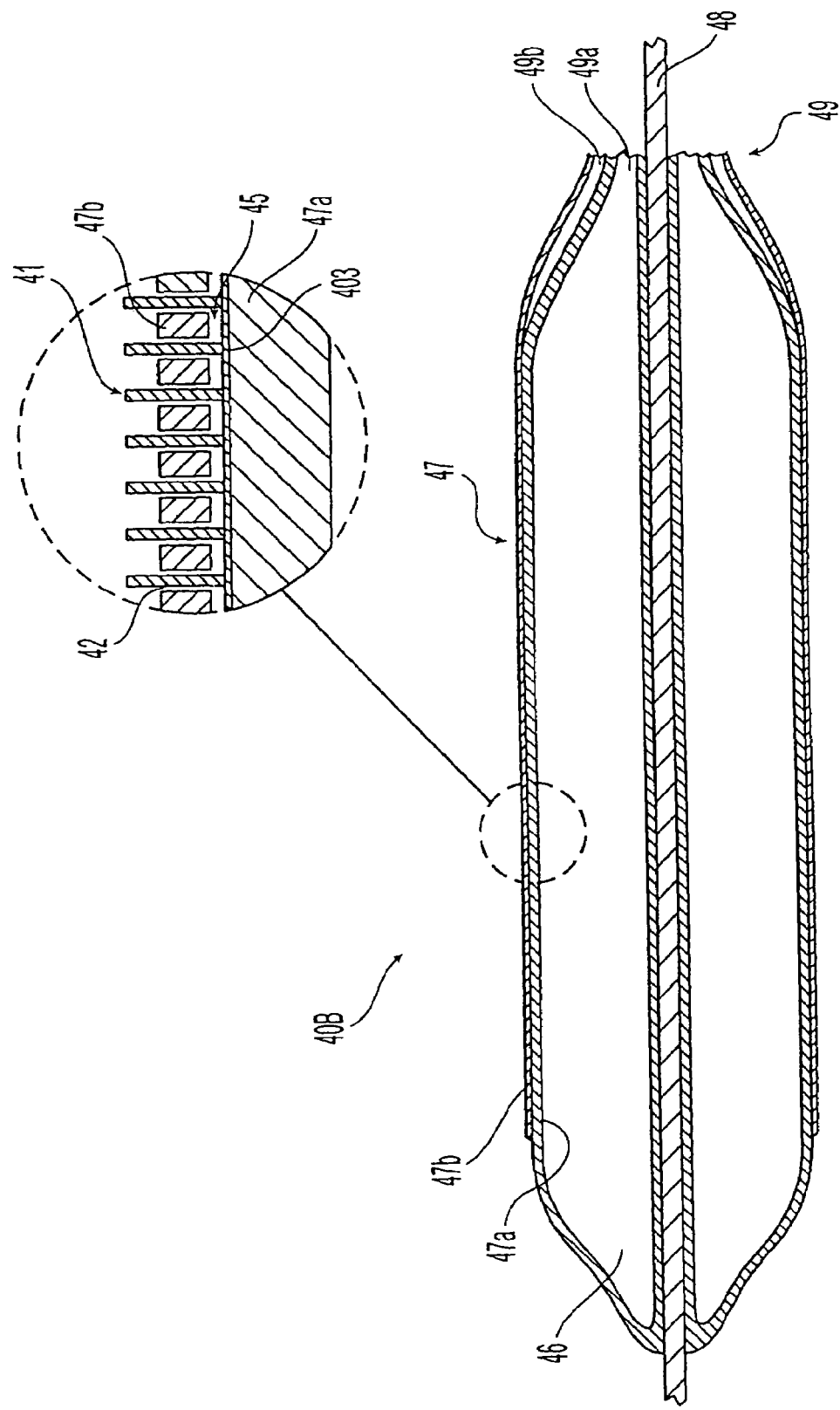

FIG. 4B shows another embodiment of an apparatus of the present invention. A plurality of solid micro-needles 41 are disposed upon a plate 403. The plate 403 is disposed between an outer layer 47b and an inner layer 47a of an balloon wall 47 of a balloon 40B. The outer layer 47b has a plurality of pores 42. The micro-needles 41 are positioned such that they project through the outer layer 47b and are disposed on an outer surface of the balloon. The plate 403 and the outer layer 47b define a compartment 45, which contains a biologically active material. The biologically active material is placed into the compartment 45 using a first catheter lumen 49b. The balloon 40B of this embodiment is inflated in a body lumen by inserting a liquid or gas into an inflation compartment 46 using an inflation lumen 49a of the catheter 49 having a guidewire 48. Upon inflation, the micro-needles 41 contact a surface of the body lumen piercing the surface and create micro- or nano-pores in the surface. The biologically active material is expelled from the pores 42 and is delivered into the micro- or nano-pores created by the micro-needles 41. After the biologically active material is delivered, the balloon is deflated and removed from the body lumen.

Figure 5A:
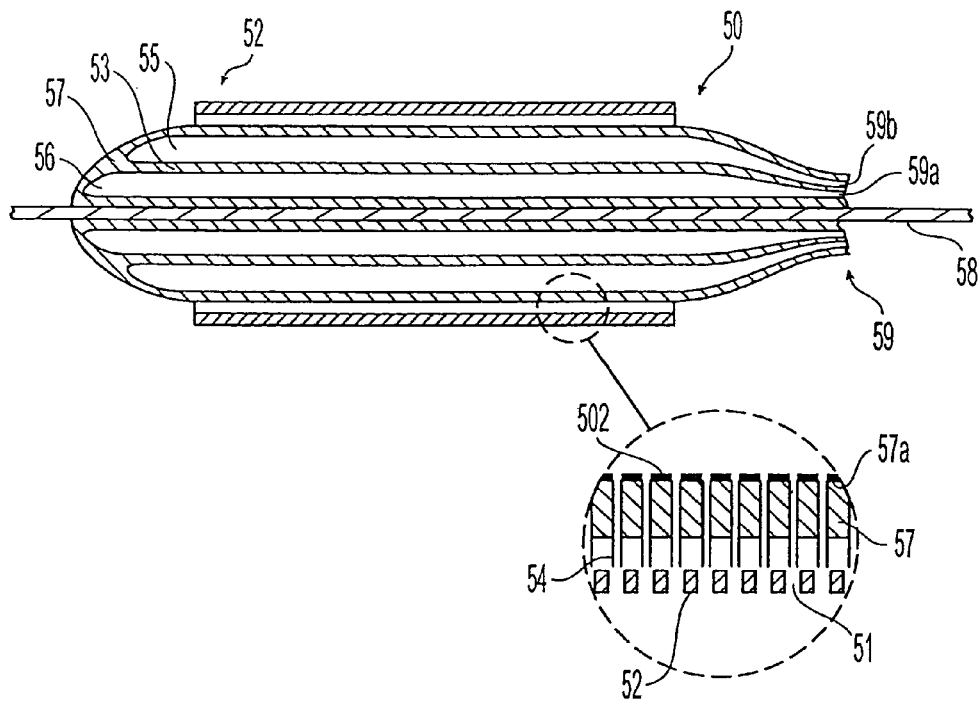
FIGS. 5A and 5B depict cross-sectional views of another embodiment of a balloon catheter of the invention, wherein a sheath surrounds a balloon having hollow micro-needles.
Figure 5B:
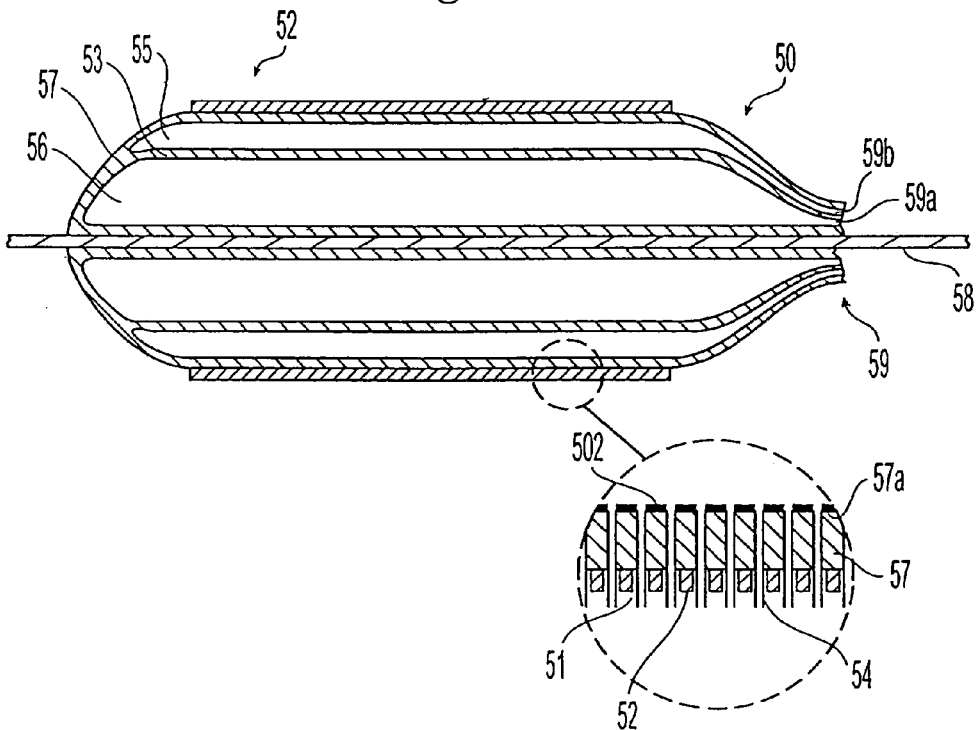

Another embodiment of the apparatus of the present invention is shown in FIGS. 5A and 5B. A balloon 50 is in its deflated state in FIG. 5A and in its inflated state in FIG. 5B. The balloon 50 has generally the same structure as that shown in FIGS. 2A and 2B except that it is surrounded by a sheath 52. The sheath is used to protect both the micro-needles and the surface of a body lumen, while the balloon with micro-needles are being positioned in or withdrawn from the body lumen. The sheath can also prevent the biologically active material from being inadvertently delivered during catheter placement or withdrawal. A plurality of micro-needles, in this case hollow micro-needles 54 having apertures, are disposed upon a plate 502, which is disposed on the inner surface 57a of a balloon wall 57. The balloon 50 comprises an interior compartment 55 which is defined by the balloon wall 57 and an interior wall 53. The micro-needles 54 project through the balloon wall 57 and are disposed upon an outer surface of the balloon. The sheath 52 has a plurality of ports or openings 51 through which the micro-needles 54 are able to project. The balloon 50 is inflated by infusing a liquid or gas into the inflation compartment 56 of the balloon 50 using an inflation lumen 59a of the catheter 59 having a guidewire 58. As the balloon 50 is inflated, the balloon wall 57 contacts the sheath 52 and the micro-needles 54 project out through the ports 51 of the sheath 52. The sheath 52 may expand by being pushed outwardly by the balloon 50 as in FIG. 5B. The micro-needles 54 contact a surface of the body lumen piercing the surface. A biologically active material, which is placed into the interior compartment 55 using a first catheter lumen 59b, is delivered, quickly and accurately without systemic leakage, through the micro-needles 54 into the body lumen. After the injection is completed, the balloon 50 is deflated, and the sheath 52 may collapse, or return to its original state. In other embodiments, a similar type of sheath can be used with a balloon catheter shown in FIG. 3. In another embodiment, the sheath 52 may not have any ports and is removed after the balloon 50 has been placed at the target area of the body lumen where the biologically active material is to be deliver.

FIG. 6A is a cross-sectional view of a balloon 60 along its longitudinal axis, and FIG. 6B is a cross-sectional view of the balloon 60 along line I-I in FIG. 6A. A portion of FIG. 6B is enlarged and referred to as FIG. 6B'. FIG. 6C shows the same portion of the balloon as in FIG. 6B' and in its inflated state. The balloon 60 has generally the same structure as that shown in FIGS. 5A and 5B except that it has solid micro-needles 64 instead of micro-needles having lumens and does not have an interior compartment. A plurality of micro-needles 64 are disposed upon a plate 602 which is disposed on the outer surface 67a of a balloon wall 67. The balloon 60 comprises an inflation compartment 66. When the balloon 60 is in its deflated state, the micro-needles 64 lay along the outer surface 67a of the balloon wall 60 and are covered by a sheath 62 as shown in FIG. 6B'. The sheath 62 has a plurality of ports or openings 61.

The balloon 60 is inflated by placing a fluid into the inflation compartment 66 of the balloon 60 using an inflation lumen 69a of the catheter 69 having a guidewire 68. As the balloon 60 is inflated, the micro-needles 64 become erect such that they protrude from an outer surface 67a of the balloon 60. Upon inflation of the balloon 60, the outer surface 67a contacts the sheath 62 and the micro-needles 64 project out through the ports 61 of the sheath 62 as shown in FIG. 6C. The sheath 62 may expand by being pushed outwardly by the balloon 60. A biologically active material may be placed on the outer surface 67a of the balloon 60 (not shown). When the micro-needles 64 contact a surface of the body lumen, piercing the surface and create micro- or nano-pores in the body lumen, the biologically active material is forced into or allowed to seep into the micro- or nano-pores created by the micro-needles 64. After a predetermined time, the balloon 60 is deflated, and the sheath 62 may collapse, or return to its original state, and those are removed from the body lumen.

In other embodiments, the balloon 60 may have an internal compartment for delivering a biologically active material, and either the micro-needles 64 have lumens or the balloon 60 is porous to allow delivery of the biologically active material.

Figure 7A:
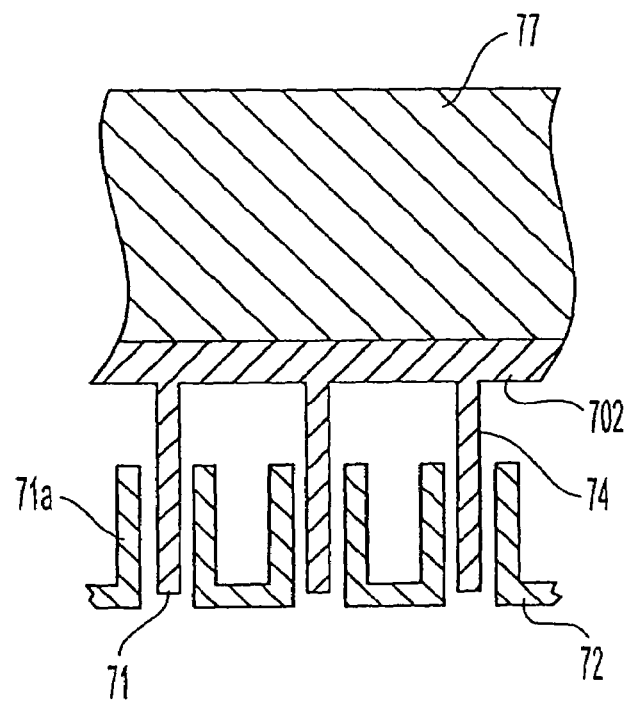
FIGS. 7A and 7B depict cross-sectional views along the longitudinal axis of a portion of another embodiment of a balloon catheter of the invention, wherein a sheath surrounds a balloon having micro-needles.
Figure 7B:
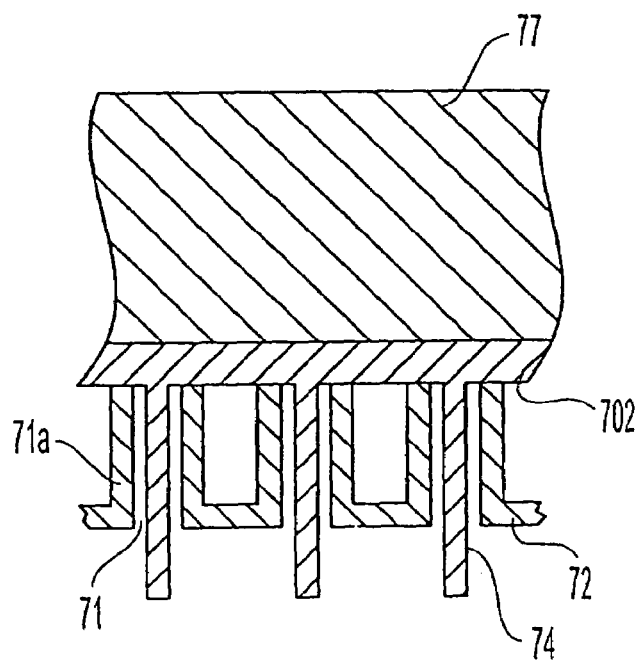

A portion of another embodiment of the apparatus of the present invention is shown in FIGS. 7A and 7B. A balloon 77 is in its deflated state in FIG. 7A and in its inflated state in FIG. 7B. Since the balloon 77 has generally the same structure as that shown in FIGS. 5A and 5B, the figures do not show the entire balloon. In this embodiment, the sheath 72 surrounding the balloon 72 has a plurality of micro-needle-channels 71a for guiding the micro-needles 74 through the ports 71 of the sheath 72. The length of the channel 71 is shorter than that of the micro-needles 74, and the internal diameter of the channel 71 is larger than the external diameter of the micro-needles 74. As shown in FIG. 7A, when the balloon 77 is deflated, only a part of the micro-needles 74 are surrounded by the channels 71a. As the balloon 77 is inflated, the micro-needles 74 are guided by the channels 71a through the ports 71. When the balloon 77 is in its most inflated state, as shown in FIG. 7B, the tips of the micro-needles 74 project out through the ports 71 and contact the surface of the body lumen piercing its surface.

Figure 8A:
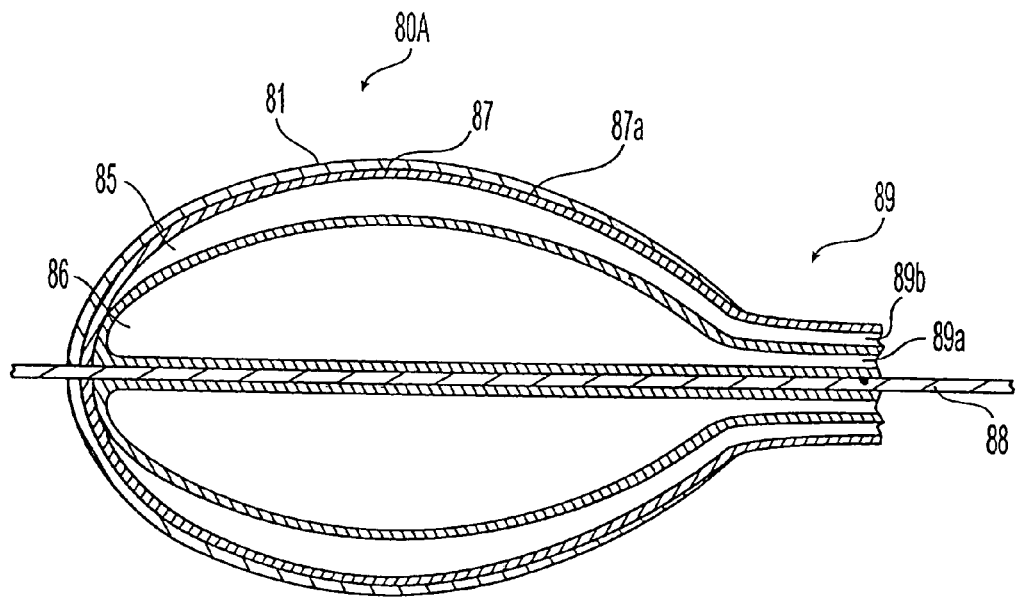
FIGS. 8A and 8B depict cross-sectional views along the longitudinal axis of other embodiments of balloon catheters of the invention where a shockwave generator is used to deliver the biologically active material.
Figure 8B:
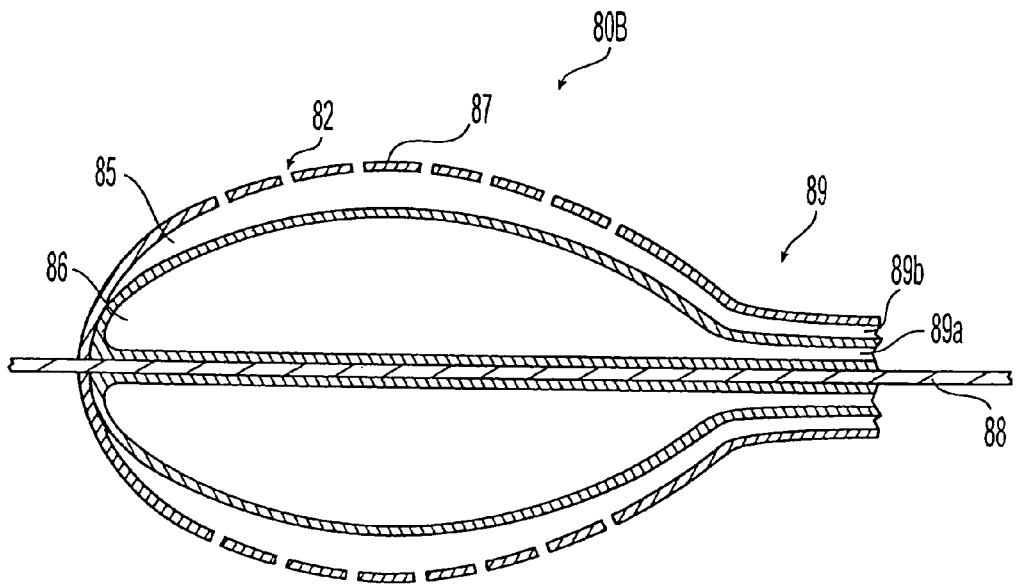
Figure 9C:
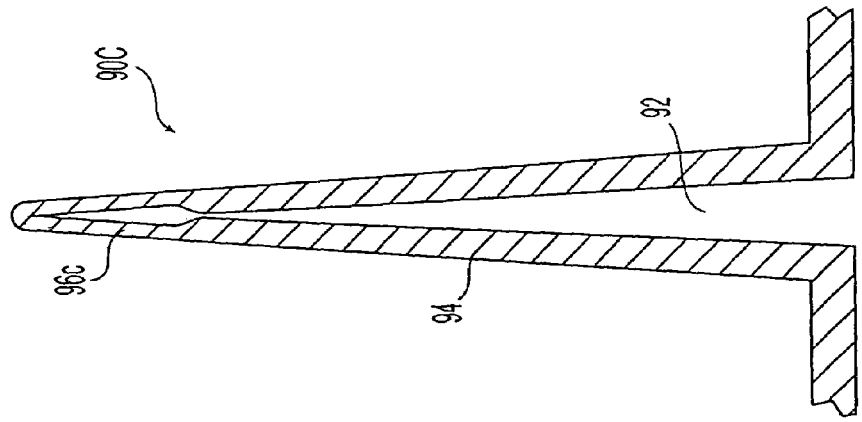
FIGS. 9A, 9B and 9C each depict an embodiment of a micro-needle which is capable of being ruptured.
Figure 9B:
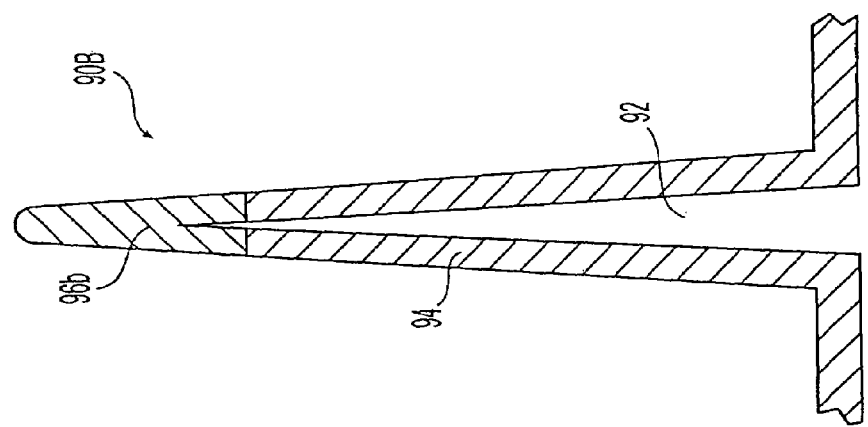
Figure 9A:
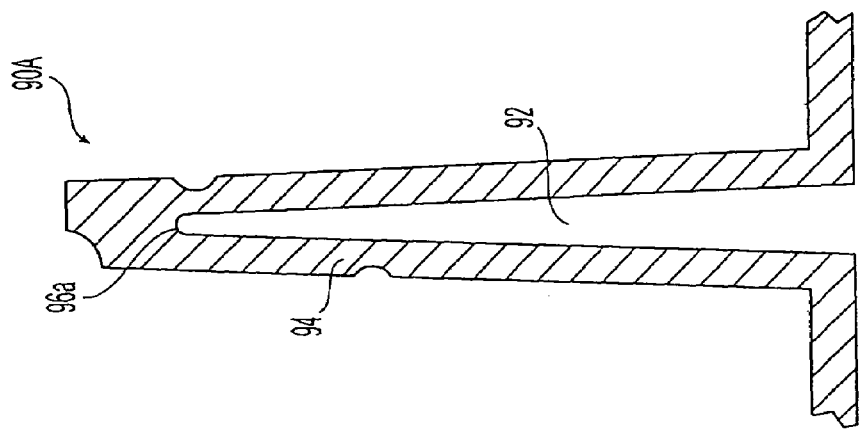

FIGS. 8A and 8B depict cross-sectional views of another embodiment of the invention in which a shockwave source or a shockwave generator is employed. In the embodiment shown in FIG. 8A, the balloon 80A is disposed upon a distal portion of a catheter 89 having a guidewire 88. The balloon 80A has an inflation compartment 86 and an interior compartment 85 for containing a fluid. The inflation compartment is in fluid communication with an inflation lumen 89a of the catheter 89 and the interior compartment 85 is in fluid communication with a first catheter lumen 89b. A shockwave source (not shown in FIG. 8A; see FIG. 1, number 13) can be disposed upon a proximal portion of the catheter 89. The biologically active material is contained in a polymer coating 81 on the outer surface 87a of the balloon 80A. When the balloon 80A is positioned and inflated to contact a surface of the body lumen, a shockwave is generated by the source and is propagated through the first catheter lumen 89b and through the interior compartment 85. The shockwave disrupts the cell lipid bilayer of the cells at the body lumen and can simultaneously create a compressive force which delivers the biologically active material through the disrupted cell lipid bilayer into cell cytoplasm. A shockwave is a wave formed of a traveling zone of pressure within a fluid.

In FIG. 8B, the balloon 80B is disposed upon a distal portion of a catheter 89 having a guidewire 88. The balloon 80B has an inflation compartment 86 and an interior compartment 85. The inflation compartment 86 is in fluid communication with an inflation lumen 89a of the catheter 89 and the interior compartment 85 is in fluid communication with a first lumen 89b of the catheter. The interior compartment 85 contains a biologically active material that is preferably suspended or dissolved in a fluid. Preferably, the balloon wall 87 contains a plurality of pores 82. When the balloon 80B is positioned and inflated to contact a surface of the body lumen, the biologically active material is infused into the interior compartment 85 and slowly expelled from pores 82 in the balloon wall 87. A shockwave is generated by a shockwave generator and propagates through the first lumen 89b and the biologically active material in the interior compartment 85. The shockwave disrupts the cell lipid bilayer of the cells in the body lumen and also creates a compressed force which delivers the biologically active material through the disrupted cell lipid bilayer into cell cytoplasm.

Further, in another embodiment, a balloon catheter, for either expelling a biologically active material through pores in a balloon wall or delivering the biologically active material contained in a polymer coated on the outer surface of the balloon, is inserted in a body lumen of an afflicted area. Then, a shockwave source generates a shockwave from outside the patient's body, wherein the shockwave is focused on a body lumen. The shockwave disrupts the cell lipid bilayer of the cells in the body lumen and also creates a compression force which delivers the biologically active material through the disrupted cell lipid bilayer into cell cytoplasm.

The following is a more detailed description of suitable materials and methods useful in producing and using the apparatus of the invention.

One can use the apparatus of the present invention to apply a biologically active material to a surface of a body lumen.

The term "biologically active material" encompasses therapeutic agents, such as drugs, and also genetic materials and biological materials. The genetic materials mean DNA or RNA, including, without limitation, of DNA/RNA encoding a useful protein stated below, intended to be inserted into a human body including viral vectors and non-viral vectors. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor α and β, platelet derived endothelial growth factor, platelet derived growth factor, tumor necrosis factor α, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progentitor cells) stem cells (e.g., mesenchymal, hematopoietic, neuronal), pluripotent stem cells, fibroblasts, macrophage, and satellite cells.

Biologically active material also includes non-genetic therapeutic agents, such as:
  anti-thrombogenic agents such as heparin, heparin derivatives, urokinase, and PPack (dextrophenylalanine proline arginine chloromethylketone);
  anti-proliferative agents such as enoxaprin, angiopeptin, or monoclonal antibodies capable of blocking smooth muscle cell proliferation, hirudin, and acetylsalicylic acid, amlodipine and doxazosin;
  anti-inflammatory agents such as glucocorticoids, betamethasone, dexamethasone, prednisolone, corticosterone, budesonide, estrogen, sulfasalazine, and mesalamine;
  antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives;
  anesthetic agents such as lidocaine, bupivacaine, and ropivacaine;
  anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;
  vascular cell growth promotors such as growth factors, Vascular Endothelial Growth Factors (FEGF, all types including VEGF-2), growth factor receptors, transcriptional activators, and translational promotors;
  vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms;
  anti-oxidants, such as probucol;
  antibiotic agents, such as penicillin, cefoxitin, oxacillin, tobranycin
  angiogenic substances, such as acidic and basic fibrobrast growth factors, estrogen including estradiol (E2), estriol (E3) and 17-Beta Estradiol; and
  drugs for heart failure, such as digoxin, beta-blockers, angiotensin-converting enzyme (ACE) inhibitors including captopril and enalopril.
  The biologically active material can be used with (a) biologically non-active material(s) including a solvent, a carrier or an excipient, such as sucrose acetate isobutyrate (SABER™ commercially available from SBS) ethanol, n-methyl pymolidone, dimethyl sulfoxide, benzyl benxoate and benzyl acetate.

The device of the present invention can be used to apply the biologically active material to any surface of a body lumen where a catheter can be inserted. Such body lumen include blood vessels, urinary tract, coronary vasculature, esophagus, trachea, colon, and biliary tract.

The present invention is generally directed to a balloon catheter device that includes an elongate, flexible catheter which extends along a longitudinal axis between a proximal end and distal end. The catheter includes an outer wall which surrounds an interior passageway, or a lumen which extends along the longitudinal axis from the proximal end. Any catheter of the type generally in use can be used for the present invention. The catheter can be extruded from a polymer, such as polyethylene, polyamides, polyimides, PEBAX or similar material.

The catheter of the present invention may have more than one lumen including one for liquid or gas for inflating the balloon and one or more lumen(s) for delivering the biologically active material(s). Preferably, the biologically active material is dissolved or suspended in a fluid such as a liquid or gas. Also, the catheter can have one or more lumen(s) for guide wire(s). The guide wire(s) may extend through the whole catheter shank and balloon. Alternatively, a guide wire may be disposed outside the catheter and extends through an inner lumen only in the area of the balloon as shown in U.S. Pat. No. 5,154,725. Also, the catheter can include a lumen for blood perfusion.

A balloon is disposed coaxially about the catheter on the distal portion of the catheter. A material for the balloon of the type generally in use can be employed for the present invention. Non-limiting examples for the balloon material include polyethylene terephthalate (PET), polyamides, polyimides, PVC, polyurethanes and similar materials. In one embodiment of the present invention, the balloon has a porous balloon wall, i.e., the balloon has a plurality of pores through which the biologically active materials can travel to the place of delivery or afflicted area.

In another embodiment, the balloon outer surface has a polymer coating containing a biologically active material. Hydrogel polymers are often used to contain the biologically active material and are disclosed in U.S. Pat. No. 5,304,121, PCT publication WO95/03083 and U.S. Pat. No. 5,120,322 which are incorporated by reference. However, a non-hydrogel, such as proteins, synthetic and natural polymers, lipids, and micro-spheres, can be also used for the present invention. The coating may be formed by an appropriate method known in the art.

The balloons of the present invention can have one or more compartment(s) including an inflation compartment. When the balloon has a coating of a polymer containing a biologically active material on its outer surface, the balloon may have only an inflation compartment, i.e., a compartment for containing liquid or gas for inflating the balloon. Also, when the balloon is used to contain the biologically active material, the balloon may have only one compartment which is for both containing the inflation gas/liquid for inflation of the balloon and containing the biologically active material. When the balloon has more than one compartment, one of the compartments can be used for inflation of the balloon, and the other(s) can be used for containing the biologically active material. The balloon compartment for inflation is preferably located closer to the center of the balloon than the compartment(s) for containing the biologically active material which is/are preferably located directly inside of the balloon wall or is in fluid communication with either pores or micro-needles in the balloon. However, the compartment for containing the biologically active material does not have to necessarily surround the whole inflation compartment.

In one embodiment of the present invention, the balloon includes a plurality of micro-needles. As shown in FIGS. 2A, 2B, 3, 4A, 4B, 5A, 5B, 6A-C, 7A and 7B the needles can be disposed on a plate which is then disposed on or in the balloon wall. As stated above, the term "micro-needle" is a term of art, and generally construed as a needle of a diameter at most 100 μm and of a length at most 1 mm. An appropriate size of the micro-needles depends on the thickness of the balloon, the size of body lumen where the balloon catheter is introduced, how deep the targeted site is located from the top of the body lumen surface, and also the size of the biologically active material to be delivered. Generally, the outer diameter of the micro-needles is between about 10 nm and about 100 μm, preferably about 10 μm and below. The length of the micro-needles is typically between about 1 μm and about 1 mm, preferably about 10 μm and about 500 μm, more preferably between about 30 μm and about 200 μm. The minute size of the micro-needles will permit inter-cell penetration at controllable depths minimizing tissue damages. Furthermore, the balloon can include micro-needles of different sizes, i.e., diameters and/or length.

The micro-needles may be solid or porous, and hollow or non-hollow, i.e., solid. The term "porous" means having sufficient pores or voids where fluid and/or solid materials can pass through. The hollow micro-needle may have a tip having an aperture connected to a lumen through the micro-needle or a porous tip having a plurality of pores where at least one lumen running through the micro-needle is connected to one of the pores. The porous tips allow radial distribution of biologically active material from an individual micro-needle.

The micro-needles can be ruptured. When a micro-needle is capable of being ruptured, the micro-needle preferably has at least one weak spot which is easily broken to give an opening without creating any debris. FIGS. 9A, 9B and 9C each depict a cross-sectional view along the longitudinal axis of embodiments of micro-needles capable of being ruptured. The micro-needles 90A, 90B and 90C, have an interior lumen 92. The wall of the needle 94 has at least one weak spot 96*a*, 96*b* and 96*c* which breaks upon application of a triggering energy or triggering source to the micro-needles. Upon rupture, an opening in fluid communication with the needle lumen 92 is formed. In FIGS. 9A and 9C, the weak spots 96*a* and 96*c* are spots where a part of the needle wall 94 is thinner than the rest of the needle wall. In FIG. 9B, the weak spot 96*b* is a tip where the needle wall 94 is made of a material which is weaker than that from which the rest of the needle wall is made. In another embodiment, micro-needles have an aperture which is weakly sealed with a quickly dissolving, bioabsorbable material.

The rupturing of the micro-needles can be triggered by various sources, such as a shockwave, ultrasound energy, radio-frequency, light, temperature and other energy conducting sources, such as those used for detaching the coils disclosed in U.S. Pat. No. 5,569,245 to Guglielmi, which are incorporated by reference. Examples of suitable ultrasound energy are disclosed in U.S. Pat. No. 6,001,069 to Tachibana et al. and U.S. Pat. No. 5,725,494 to Brisken, PCT publications WO00/16704, WO00/18468, WO00/00095, WO00/07508 and WO99/33391, which are all incorporated by reference. The triggering source, such as a shockwave, generates the needed pressure to rupture the micro-needle tips and to expel a dose of the biologically active material at sufficient velocity to penetrate the cell lipid bilayer of the cells of the body lumen.

The micro-needles capable of being ruptured may be made from a bioabsorbable material, such as poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycotic acid), poily(D, L-lactic acid), poly(glycotic acid-co-trimethylene carbonate), polyphosphoester, polyphosphoester urethane, poly(amino acids), cyanoacrylates, poly(trimethylene carbonate), poly(iminocarbonate), copoly(ether-ester) (e.g. PEO/PLA), polyalkylene oxalates, polyphosphazenes and biomolecules such as fibrin, fibrinogen, cellulose, starch, collagen and hyaluronic acid.

When the micro-needles are non-hollow, i.e., solid, the micro-needles may have gutters on their exterior surface along their longitudinal axis. The biologically active material can travel along the gutter to the afflicted area by capillary action. A biologically active material is either contained in a coating on the surface of the balloon or expelled from the pores in the balloon wall, and is delivered into the micro- or nano-pores, i.e., the punctures created by the micro-needles. Also, hollow micro-needles and solid micro-needles can be used together in a single balloon.

The micro-needles of the present invention can be made from a number of appropriate materials, such as metals, ceramics, semiconductors, organics, polymers and composites. Preferred materials are stainless steel, nickel, iron, tin, chromium, copper, gold, titanium, alloys of these or other metals, glass, silicon, silicon dioxide and polymers, such as PET, polyurethane, PVC, polyamides, polycarbonates, polyethylene, and high-density UPE. Bioabsorbable polymers are preferable in case the micro-needles are broken and left in a body lumen or tissue.

The micro-needles are micro-fabricated by processes known to the skilled artisans, e.g., etching techniques, such as photoresist, wet, and dry removal; electroplating and electroless plating; diffusion processes, such as boron, phosphorus, arsenic, and antimony diffusion; film deposition, such as evaporation, sputtering, chemical vapor deposition (CVD), epitaxy, electroplating, screen printing, lamination stereolithography, laser machining, and laser ablation; lithography; thermal oxidation of silicon. Those methods are explained in greater detail in PCT publication WO99/64580 and Micromechanical Devices for Intravascular Drug Delivery, Michael L. Reed, Journal of Pharmaceutical Sciences, vol. 87, no. 11, (November 1998), 1387-1394 which are incorporated by reference.

For example, metal micro-needles disposed on a plate can be made by physical vapor deposition of appropriate metal layers on solid needle forms made by silicon, by embossing, or by injection molding. The silicon solid needle form can be made, e.g., by using thermal oxidation of silicon, a wafer is thermally oxidized to grow a thin layer of $SiO_2$, and then, the $SiO_2$ layer is patterned by photolithography. When the $SiO_2$ layer is immersed in an aqueous solution of potassium hydroxide, the wafer surface not covered with $SiO_2$ is etched, and the areas covered with $SiO_2$ becomes the solid micro-needles.

Particularly, methods for making hollow micro-needles disposed on a plate is also known in the art (see WO99/64580). Examples for such methods are a micromold plating method:

(1) A photo-defined mold is first produced by, e.g., spin casting a thick layer, about 150 μm, of an epoxy onto a substrate, such as glass or silicon, that has been coated with a thin sacrificial layer (e.g., copper laminate), typically about 10 to 50 nm thick. A plurality of cylindrical holes are then photolithographically defined through the epoxy layer.

(2) The sacrificial layer, is partially removed at the bottom of the cylindrical holes in the photoresist by e.g., wet etching.

(3) A seed layer, such as Ti/Cu/Ti (e.g., 30 nm/200 nm/30 nm) is conformally DC sputter-deposited onto the upper surface of the epoxy mold and onto the side walls of the cylindrical holes. The seed layer should be electrically isolated from the substrate.

(4) One or more electroplatable metals or alloys, such as Ni, Ni, Fe, Au, Cu, or Ti are electroplated onto the seed layer.

(5) The surrounding epoxy is removed, leaving a plate having hollow micro-needles disposed upon it.

Tapered hollow micro-needles can be made in the same way by making a tapered mold e.g., by using a mold-insert or laser-ablated mold. Porous micro-needles can be made either by etching a porous material or rendered solid micro-needles porous, for example, by means of electrochemical oxidation.

Various methods can be used to displace the plate upon which the micro-needles are disposed, to the balloon. In one embodiment, the plate is secured to the inner surface of the balloon wall in a manner such that the plate and balloon wall will move as a single unit upon expansion. Furthermore, a balloon having micro-needles can be prepared by, first forming a balloon by a conventional method and then attaching plates with micro-needles by heat or chemical treatment or using an adhesive. Also, instead of using heat or chemical treatment, the plate can be secured to the balloon by covering it with another balloon or a sheath. In one embodiment, a second balloon is formed over a first balloon on which a plate with micro-needles is attached, and the micro-needles project through the second balloon. In another embodiment, the plate is secured to the inner surface of the balloon wall so that the micro-needles are retracted when the balloon is deflated and will protrude through the balloon wall when the balloon is inflated. The balloon wall can be punctured by the micro-needles or it can have openings for micro-needles to protrude through. Also, the plate can be located within the balloon wall, such that it is sandwich between two layers of material that make up the balloon wall.

Alternatively, a balloon having micro-needles can be prepared from a polymer sheet having micro-needles. A sheet having micro-needles can be prepared by attaching a plate having micro-needles to a polymer sheet by, e.g., heat or chemical treatment or using an adhesive prior to formation of a balloon. In one embodiment, instead of heat or chemical treatment, the plate having micro-needles can be pressed to the polymer sheet so that the micro-needles project through the polymer sheet. The plate may be warmed so that the micro-needles can easily project through the polymer sheet. In another embodiment a second layer of balloon wall material is attached to the underside (i.e., side without needles) of the plate. Once the plate is attached to the polymer sheet, the sheet is folded to form a balloon by a conventional method.

The micro-needles can be oriented perpendicular or at an angle to the outer balloon surface. Hollow micro-needles may be in fluid communication with an internal compartment of the balloon. The micro-needles may be distributed uniformly within the area of the balloon surface which contacts the body lumen when the balloon is expanded. Alternatively, the micro-needles can be disposed upon a limited area of the balloon surface, such as its one half side or its center. The number of the micro-needles distributed in a given area of the balloon depends on the targeted tissue. Generally, about one micro-needle per ten (10) cells is preferred. Typically, the number of the micro-needles is more than about ten (10) per $cm^2$, preferably between about $1 \times 10^2$ and about $1 \times 10^6$, more preferably between about $1 \times 10^3$ and about $1 \times 10^5$ per $cm^2$. The numerous micro-needles ensure uniform delivery over the area of targeted tissue.

In one embodiment of the device of the present invention, a sheath (see FIG. 5) surrounding at least a part of the balloon is included. The sheath of the present invention can be made from various materials, for example, metals, such as nitinol, platinum, stainless steel, and various alloys, and polymers. Preferably, the sheath is expandable; and the expandable sheath may be attached to the balloon so that the sheath expands as the balloon expands and collapses as the balloon is deflated.

Furthermore, the sheath has a plurality of ports. The ports can be any shape, such as a round, oval or square hole and a slit, so long as the micro-needles can project through the ports. The sheath can also be formed of a mesh. Generally, the thickness of the sheath is between about 0.01 and about 0.1 mm.

Alternatively, a sheath without ports may be made of a material which is capable of being punctured by the micro-needles, such as a polymer. When the balloon is inflated, the micro-needles disposed upon the balloon puncture the sheath and project through the sheath. Examples of polymers suitable for the sheath are polyurethanes, polyesters, PTFE and FEP; polyethylene and nylon are preferable. One of ordinary skill can select the polymer material and thickness for the sheath as well as the material and sizes of the needles in order to obtain the desired results.

Moreover, another embodiment of the device of the present invention involves a shockwave generator for delivery of the biologically active material to the body lumen (see FIGS. 6A and 6B). Shockwave sources known in the art can be used for the present invention; preferably the source generates a shockwave having enough energy to disrupt the cell lipid bilayer of the cells in the body lumen. Examples of such sources are disclosed in U.S. Pat. Nos. 5,233,972, 5,374,236, and 4,610,249. Shockwave sources are used extensively in lithotripsy, i.e. methods of treating kidney stones. The same types of sources used in such technique can be applied to the present invention. Generally the energy of the shockwave used is less intensive than that used in lithotripsy. Also, the area of the body lumen exposed to the shockwave in the present invention is smaller than that in lithotripsy. To disrupt the cell lipid bilayer, generally, the shockwave should have a pressure of between about 10 atm and about 5,000 atm, preferably between about 75 atm and about 150 atm pressure are useful. Also, the shockwave should be applied for relatively short periods of time, such as between about 1 nsec and about 1 msec.

In one embodiment, wherein the biologically active material is contained in a polymer coating on the balloon's exterior surface, when the balloon is positioned and inflated to contact a surface of the body lumen, the shockwave is created at the proximal portion of the catheter. The shockwave travels to the distal portion of the catheter where the biologically active material is to be delivered, and disrupts the cell lipid bilayer of the cells in the body lumen. The shockwave creates a compression force which delivers the biologically active material through the disrupted cell lipid bilayer into the cell cytoplasm. The balloon in this embodiment may also have the micro-needles discussed above.

A balloon catheter of the present invention can be used with a shockwave source which is not attached to the catheter. When the balloon catheter contacts a surface of a body lumen, the shockwave source is focused on the surface from outside the patient's body. Skilled artisans in the art know how to focus on a surface of a body lumen.

In another embodiment of the present invention, the balloon may have micro-needles without any openings but capable of being ruptured as explained above and the micro-needles have an interior lumen in fluid communication with an interior compartment of the balloon, which contains a biologically active material. When the balloon is positioned and inflated, micro-needles contact a surface of the body lumen piercing it. A triggering source is applied to rupture the micro-needles to deliver the biologically active material from the interior compartment.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. An apparatus for delivering a biologically active material to a body lumen comprising:
   a catheter having a distal portion and a proximal portion;
   a balloon, having a balloon wall including a layer defining an outer surface and an inner surface, disposed at the distal portion of the catheter; and
   a plurality of micro-needles disposed upon the outer surface of the balloon,
   wherein the micro-needles are capable of contacting the body lumen to deliver the biologically active material to the body lumen; and the micro-needles are disposed upon a plate, which is attached to the inner surface of the layer of said balloon wall in a manner such that the micro-needles project through the layer of the balloon wall.

2. The apparatus of claim 1, wherein the plate is attached to the balloon in a manner such that the micro-needles are capable of being retracted when the balloon is deflated and capable of being projected through the balloon wall when the balloon is expanded.

3. The apparatus of claim 1, wherein the plate is solid.

4. The apparatus of claim 1, wherein the plate is porous.

5. The apparatus of claim 1, wherein the balloon wall also includes an additional layer and the plate is between the layer and the additional layer.

6. The apparatus of claim 1, wherein the biologically active material is contained in the layer of the balloon wall.

7. The apparatus of claim 1, wherein the balloon includes a first compartment for storing the biologically active material and a second compartment for inflating the balloon.

8. An apparatus for delivering a biologically active material to a body lumen comprising:
   (a) a catheter having a distal portion, a proximal portion and a first lumen therethrough;
   (b) a balloon disposed at the distal portion of the catheter, wherein the balloon has an interior compartment in fluid communication with the first lumen of the catheter; the balloon has an outer surface having a plurality of micro-needles disposed thereon; and each micro-needle of said plurality of micro-needles has a lumen in fluid communication with the interior compartment and wherein the micro-needles are capable of being ruptured; and
   (c) a triggering source to rupture the micro-needles when activated to deliver the biologically active material from the interior compartment of the balloon through the micro-needle lumens to the body lumen, wherein the triggering source is selected from the group consisting of a shockwave, ultrasound energy and energy source for delivering a detachable coil.

9. The apparatus of claim 8, wherein the balloon outer surface is part of a balloon wall, and the micro-needles are disposed upon a plate attached to the balloon wall in a manner such that the micro-needles project through the balloon wall.

10. The apparatus of claim 8, wherein the triggering source is disposed at the proximal portion of the catheter.

11. The apparatus of claim 8, wherein the triggering source is a shockwave.

* * * * *